US009827432B2

(12) United States Patent
Wu (10) Patent No.: US 9,827,432 B2
(45) Date of Patent: Nov. 28, 2017

(54) HEADREST STRUCTURE (71) Applicant: Chun-Hung Wu, New Taipei (TW)

(72) Inventor: Chun-Hung Wu, New Taipei (TW)

( * ) Notice: Subject to any disclaimer, the term of this patent is extended or adjusted under 35 U.S.C. 154(b) by 0 days.

(21) Appl. No.: 14/693,217

(22) Filed: Apr. 22, 2015

(65) Prior Publication Data
US 2015/0224329 A1 Aug. 13, 2015

(30) Foreign Application Priority Data

Oct. 8, 2014 (TW) .............................. 103135117 A
Mar. 24, 2015 (CN) ..................... 2015 2 0167459 U (51) Int. Cl.
A61N 1/00 (2006.01)
A61N 1/39 (2006.01)
B60N 2/48 (2006.01)
A61N 1/04 (2006.01)

(52) U.S. Cl.
CPC ........... A61N 1/3968 (2013.01); A61N 1/046 (2013.01); A61N 1/39 (2013.01); B60N 2/4876 (2013.01)

(58) Field of Classification Search
CPC ........ A61N 1/046; A61N 1/39; A61N 1/3968; B60N 2/4876
See application file for complete search history.

(56) References Cited

U.S. PATENT DOCUMENTS

| 7,543,887 | B2 | 6/2009 | Tatlock | |
| 9,095,231 | B2 * | 8/2015 | Abdo | A47G 9/1009 |
| 2002/0169482 | A1 | 11/2002 | SerVaas | |
| 2004/0212745 | A1 | 10/2004 | Chang | |
| 2005/0085799 | A1 | 4/2005 | Luria et al. | |
| 2005/0099547 | A1 | 5/2005 | Vitito | |
| 2006/0208020 | A1 | 9/2006 | Albert et al. | |
| 2008/0122269 | A1 | 5/2008 | Tatlock | |
| 2008/0284219 | A1 | 11/2008 | Koontz, II et al. | |
| 2014/0039359 | A1 * | 2/2014 | Madanat | A61N 1/39 601/15 |
| 2015/0224329 | A1 | 8/2015 | Wu | |

FOREIGN PATENT DOCUMENTS

| DE | 102004063564 A | 7/2006 |
| DE | 102005035625 | 2/2007 |
| DE | 102012004377 | 11/2012 |
| DE | 102012004377 A1 | 11/2012 |
| JP | 2002010864 | 1/2002 |
| JP | 3091897 | 11/2002 |
| JP | 3147262 | 12/2008 |
| JP | 2009107582 | 5/2009 |

(Continued)

*Primary Examiner* — Lindsey G Wehrheim
(74) *Attorney, Agent, or Firm* — Muncy, Geissler, Olds & Lowe, P.C.

(57) ABSTRACT

A headrest structure is provided and includes a body and two supporting rods. The body includes a covering cushion and an automated external defibrillator (AED). The AED is enclosed by the covering cushion. Each of the supporting rods includes a linking end and a combining end opposite to the linking end, and each of the supporting rods is connected to the body with the linking end so as to support the body. Based on this, the AED is assembled in the body to improve the applicability of the AED, so that patients experiencing cardiac arrest can be treated properly and instantly.

25 Claims, 10 Drawing Sheets

(56) References Cited

FOREIGN PATENT DOCUMENTS

| | | |
|---|---|---|
| JP | 2009107582 A | 5/2009 |
| JP | 2011219046 | 11/2011 |
| JP | 2013169909 | 9/2013 |
| JP | 2014149855 | 8/2014 |
| TW | M371559 U | 1/2010 |
| TW | 201020145 | 6/2010 |
| TW | M456823 U | 7/2013 |
| TW | M465922 U | 11/2013 |
| TW | M495968 U | 2/2015 |

* cited by examiner

HEADREST STRUCTURE

CROSS-REFERENCES TO RELATED APPLICATIONS

This non-provisional application claims priority under 35 U.S.C. §119(a) on Patent Application No. 103135117 filed in Taiwan, R.O.C. on 2014 Oct. 8 and on Patent Application No. 201520167459.0 filed in China, P.R.C. on 2015 Mar. 24, the entire contents of which are hereby incorporated by reference.

BACKGROUND

Technical Field

The instant disclosure relates to a headrest structure, and more particular to a headrest structure having an automated external defibrillator assembled therein.

Related Art

According to the American Heart Association, some 360,000 out-of-hospital cardiac arrests occur each year in the United States, largely involving middle-aged men, with a survival rate of only 9.5 percent. Patients can survive if they are given cardiopulmonary resuscitation (CPR) immediately, and their hearts are jolted back into normal rhythm with a defibrillator.

According to the American Heart Association, most sudden cardiac arrest adults are in a state of ventricular fibrillation, with their hearts ceasing to pump blood. The treatment for ventricular fibrillation is use of the defibrillation and the cardioversion procedure, namely, applying electroshock to terminate the state of ventricular fibrillation and leading the heart back into normal rhythm. It is understood that the possibility of survival decreases by about 10 percent with every minute that the defibrillation and the cardioversion procedure is delayed. Additionally, if the patient cannot be treated properly in 4 to 6 minutes, even if they can survive this cardiac arrest, their brain will suffer unrecoverable damage which may result a persistent vegetative state.

If a person can have a first-aid treatment, for example, being treated immediately with an automated external defibrillator (hereinafter, AED), or other auxiliary rescuing equipment, when experiencing sudden cardiac attack, the endangered person may be saved. The AED is a simple medical device provided mainly for non-medical personnel to rescue patients in danger of sudden death from cardiac arrest. The AED can automatically detect the cardiac dysrhythmia phenomena (including ventricular tachycardia and ventricular fibrillation), of the patient, and advise whether it is necessary to apply electroshocks to the heart of the patient. Cardiac arrests resulting from sudden cardiac dysrhythmias can be recovered with a success rate of 90 percent if electroshocks are applied to the cardiac arrest patient within one minute. In the public access defibrillation (PAD) program promoted in some countries, AEDs are widely recommended and fixedly assembled in public places.

However, the fixedly assembled AEDs are immobile, thus reducing significantly the usefulness of the AEDs. For example, in a given situation, prompt application of proper first aid treatment to a person who has passed out due to cardiac arrests is unlikely to be possible, due to the lack of AED apparatuses. Consequently, it is impossible to apply first aid procedures instantly to patients suffering cardiac disease, due to lack of a systematic planning to redesign the implementation methods and the structure of the AED.

Additionally, common human transportation methods have changed from animal transportation to mechanical transportation; transportation methods continue to develop, whether on the ground, in the ocean or above the sky. Transportation has enabled humans to travel to almost anywhere in the world. Consequently, transportation, particularly methods provided to carry people, is ubiquitous to daily life; that is, the transportations are closely connected to the movements of human beings. Consequently, assembly of high mobility AED apparatuses onto the transportations for better implementation of the AED apparatuses, is an urgent necessity.

SUMMARY

In view of this, the instant disclosure provides a headrest structure comprising a body and two supporting rods. The body comprises a covering cushion and an automated external defibrillator (hereinafter, abbreviated AED). The AED is enclosed by the covering cushion. Each of the supporting rods comprises a linking end and a combining end opposite to the linking end. Each of the supporting rods is connected to the body with the linking end so as to support the body. Accordingly, by disposing the AED in the body, the headrest structure according to the instant disclosure can be detached from the seat upon someone encountering sudden cardiac arrest, thereby improving the applicability of the AED and enabling proper treatments to be applied to the person instantly, with the application of the AED. Further, since the AED is installed to the headrest of the transportation, the AED can be found and applied promptly.

In some implementation aspects, the headrest structure further comprises a handle disposed on the body and opposite to the supporting rods.

In some implementation aspects, the headrest structure further comprises a shielding member. The shielding member comprises a pivoting portion and an abutting portion opposite to the pivoting portion. The pivoting portion is pivoted on the body and near to the supporting rods. Hence, when the shielding member is located at a shielding position, the shielding member shields the handle; while when the shielding member is located at an open position, the handle is exposed to outside with the abutting portion and the combining ends being coplanar so as to support the body to stand on the ground. Based on this, the body of the headrest structure can be isolated from the ground.

In some implementation aspects, the headrest structure further comprises a covering member connected to the end portion of the abutting portion. When the shielding member is located at the shielding position to shield the handle, the covering member is covered on one side of the body and opposite to the shielding member. When the shielding member is located at the open position to expose the handle, the abutting portion and the combining ends are coplanar so as to support the body to stand on the covering member.

In some implementation aspects, the headrest structure further comprises at least one buckling member disposed at the covering member and corresponding to the combining ends of the supporting rods.

In some implementation aspects, the AED further comprises an electroshock module, at least one auxiliary electroshock member and a control module. The electroshock module is provided to output an electroshock signal. The auxiliary electroshock member comprises at least one connecting end and at least one working end. The connecting end is detachably and electrically connected to the electroshock module. The working end is provided for contacting the electroshock point of the heart of the patient, and the electroshock signal is delivered to the electroshock point of the patient through the working end. The controlling module is electrically connected to the electroshock module so as to control the output of the electroshock signal.

In some implementation aspects, the body further comprises a display module electrically connected to the AED and selectively displayed at least one physiological parameter of the patient, at least one output parameter of the electroshock signal or the combination thereof.

In some implementation aspects, the display module comprises a signal receiving unit, a coding-decoding unit and a screen. The coding-decoding unit converts a signal received by the signal receiving unit into a video signal to display on the screen. Wherein, the supporting rods are coupled to the signal receiving unit to be the antenna of the signal receiving unit.

In some implementation aspects, the body further comprises a signal emitting member electrically connected to the AED, thereby the signal emitting member automatically emits a signal when the AED is operating. Wherein, the supporting rods are coupled to the signal emitting member to be the antenna of the signal emitting member.

In conclusion, with the headrest structure according to the instant disclosure, when somebody suddenly suffers ventricular fibrillation or the ventricular tachycardia, another person (whether their friend or rescue personnel), can use the AED in the headrest structure to apply electroshock to the patient's heart, followed by applying external cardiac massage procedures or other cardiopulmonary resuscitation procedures to give the patient first aid treatment, under which circumstances the patient's likelihood of survival are increased significantly due to proper treatment being applied to the patient before arrival in the emergency room.

Detailed description of the characteristics and the advantages of the instant disclosure is shown in the following embodiments, the technical content and the implementation of the instant disclosure should be readily apparent to any person skilled in the art from the detailed description, and the purposes and the advantages of the instant disclosure should be readily understood by any person skilled in the art with reference to content, claims and drawings in the instant disclosure.

BRIEF DESCRIPTION OF THE DRAWINGS

The instant disclosure will become more fully understood from the detailed description given herein below for illustration only, and thus not limitative of the instant disclosure, wherein.

DETAILED DESCRIPTION

Figure 1:
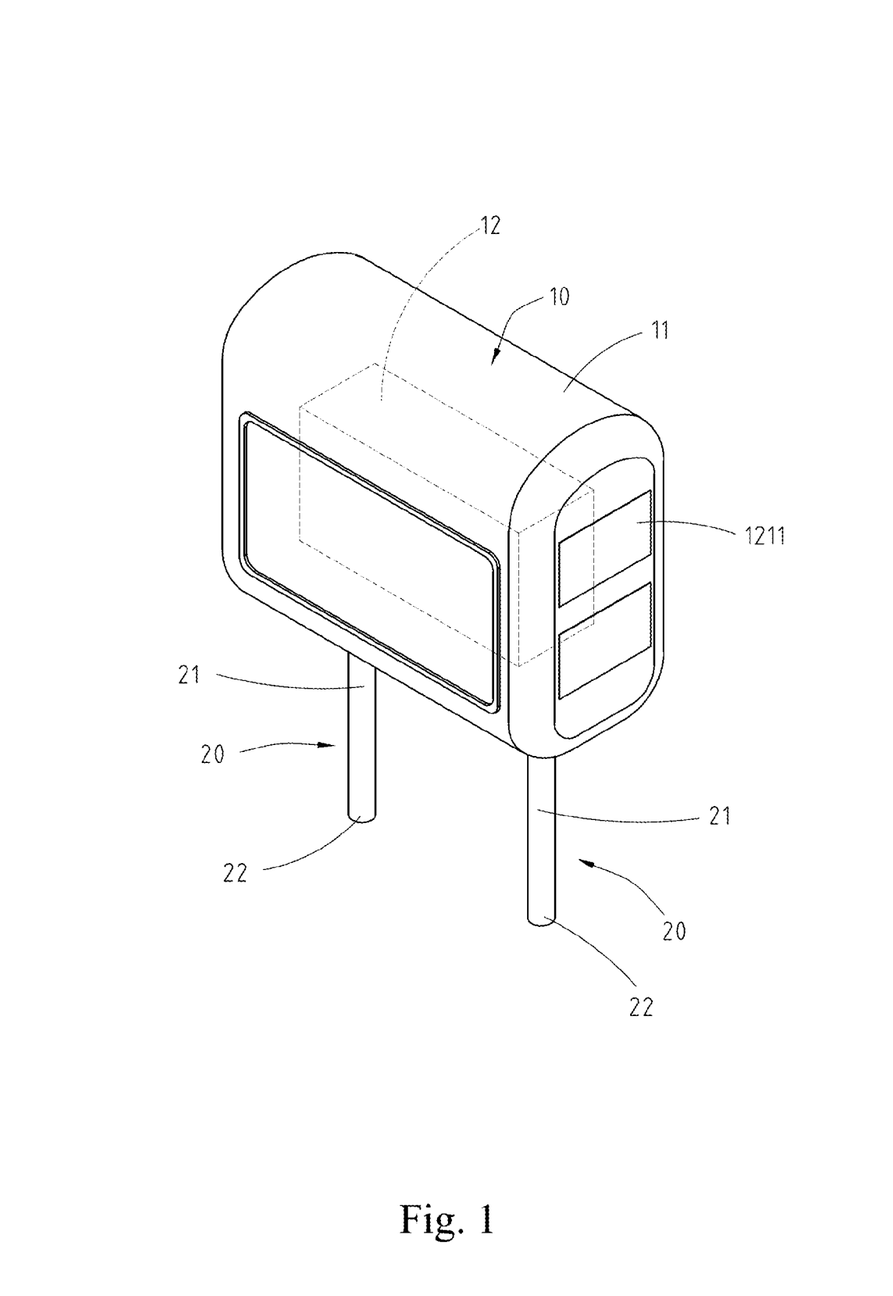
FIG. 1 is a perspective view (1) of a first embodiment of a headrest structure according to the instant disclosure.

Please refer to FIG. 1, illustrating a first embodiment of a headrest structure 100 according to the instant disclosure. FIG. 1 is a perspective view (1) of a first embodiment of a headrest structure 100 according to the instant disclosure. The headrest structure 100 is provided to be assembled to the seat or the backrest of a transportation. The transportation may be, for example, a vehicle, a ship, an airplane or a motorcycle with backrest structure; but embodiments are not limited thereto. In some implementation aspects, the headrest structure 100 is assembled to a bench chair or to the seat of a racing car in an amusement field. The headrest structure 100 comprises a body 10 and two supporting rods 20, but the number of the supporting rod 20 is not limited thereto.

The body 10 comprises a covering cushion 11 and an automated external defibrillator 12 (hereinafter, abbreviated AED). The covering cushion 11 may be made of, for example, soft materials for a user's head to lean against. The AED 12 is enclosed by the covering cushion 11 and opposite to a leaning surface of the body 10 adapted for head leaning. Therefore, the electronic components within the AED 12 can work normally at the very moment to rescue the patient even when the headrest structure 100 is severely impacted by a foreign force with the soft covering cushion 11 provided to absorb foreign impacts.

Each of the supporting rods 20 comprises a linking end 21 and a combining end 22 opposite to the linking end 21. Each of the supporting rods 20 is connected to the body 10 with the linking end 21 so as to support the body 10. The supporting rods 20 are provided to connect with the seat of the transportation for the user's head to lean against. Additionally, the combining ends 22 have engaging structure assembled thereon so as to detachably connected with the seat of the transportation. Here, the supporting rods 20 are provided to isolate the body from the ground. In addition, in this embodiment, the supporting rods 20 are substantially perpendicular to the bottom plane of the body 10, but embodiments are not limited thereto. The angle between the supporting rods 20 and the body 10 may be adjustable.

According to the instant disclosure, the AED 12 is modulized into the headrest structure 100 so as to connect with the transportation having backrest; when a person encounters cardiac arrest suddenly, proper treatments can be applied to the person instantly with the application of the AED 12.

Figure 2A:
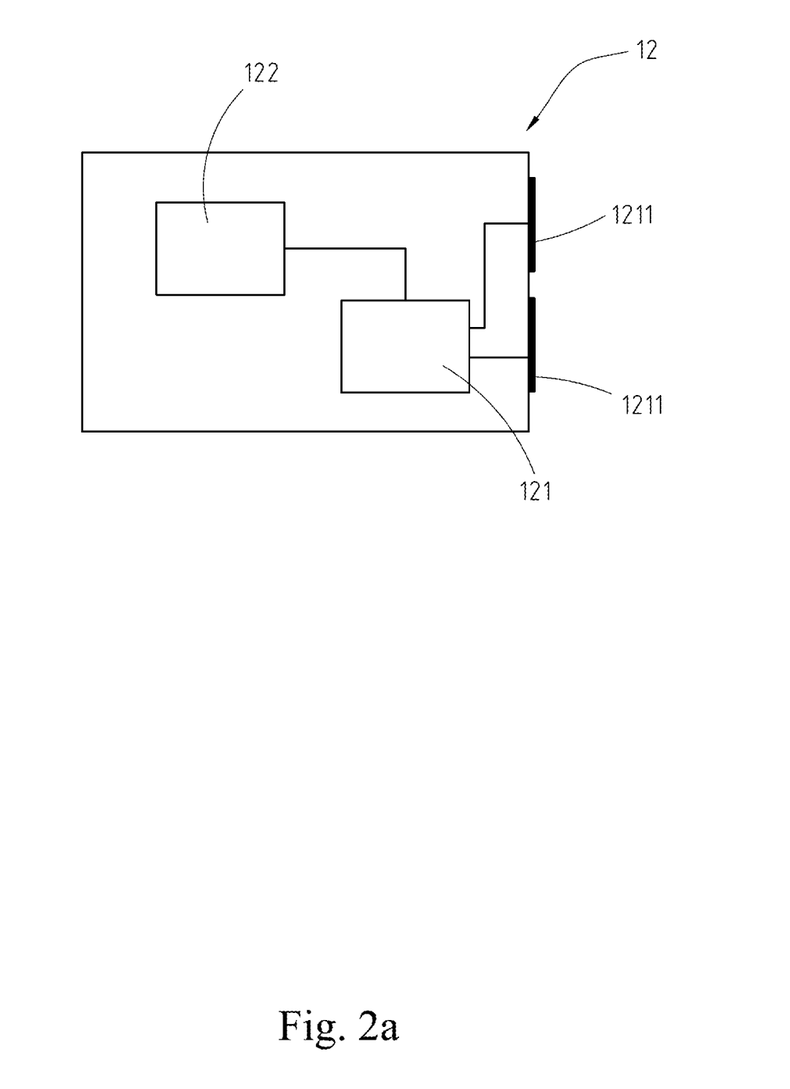
FIG. 2a is a block diagram (1) showing the automated external defibrillator of the first embodiment of the headrest structure according to the instant disclosure.

Please refer to FIG. 2a, showing a block diagram (1) of the AED 12 of the first embodiment of the headrest structure 100 according to the instant disclosure. Here, the AED 12 comprises an electroshock module 121, a plurality of conductive plates 1211 and a control module 122.

The electroshock module 121 is provided to output an electroshock signal. The conductive plates 1211 are electrically connected to the electroshock module 121 to contact with an electroshock point of the heart of a patient, so that the electroshock signal is delivered to the electroshock point of the patient through the conductive plates 1211. Based on this, the conductive plates 1211 are attached on the electroshock point of the patient's heart and an electroshock loop is formed between the patient's heart and the AED 12, thereby the electroshock signal is delivered to the patient's heart. Here, the conductive plates 1211 are made of electrically conductive materials, such as gold, platinum, silver, copper, stainless material or conductive polymers, but embodiments are not limited thereto. The control module 122 is electrically connected to the electroshock module 121 so as to control the output of the electroshock signal or the input of a physiological information of the patient. In this embodiment, the control module 122 comprises a processor and an operating module provided for controlling the processor. For example, the operating module is a plurality of solid buttons for manually or automatically controlling the intensity, the frequency, the electroshock mode, the applied times or other parameters of the electroshock signal, or for controlling the types of the physiological information to be collected from the patient, but embodiments are not thus limited thereto. In some implementation aspects, the operating module may be a plurality of or a single virtual buttons, solid toggles, knobs or may be a remote controller.

Figure 2B:
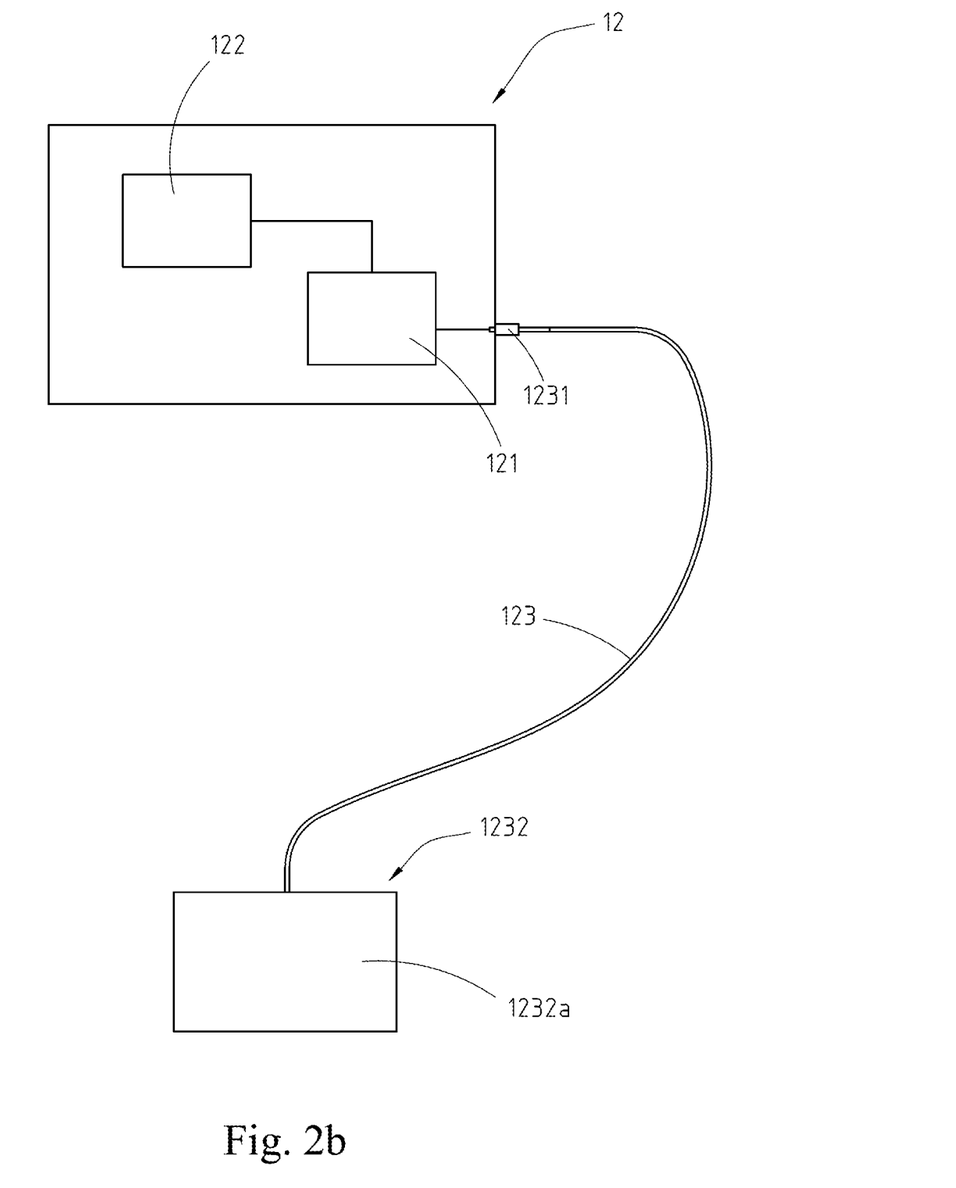
FIG. 2b is a block diagram (2) showing the automated external defibrillator of the first embodiment of the headrest structure according to the instant disclosure.

Please refer to FIG. 2*b*, showing a block diagram (2) of the AED 12 of the first embodiment of the headrest structure 100 according to the instant disclosure. Here, the AED 12 comprises an electroshock module 121, at least one auxiliary electroshock member 123 and a control module 122.

Figure 2C:
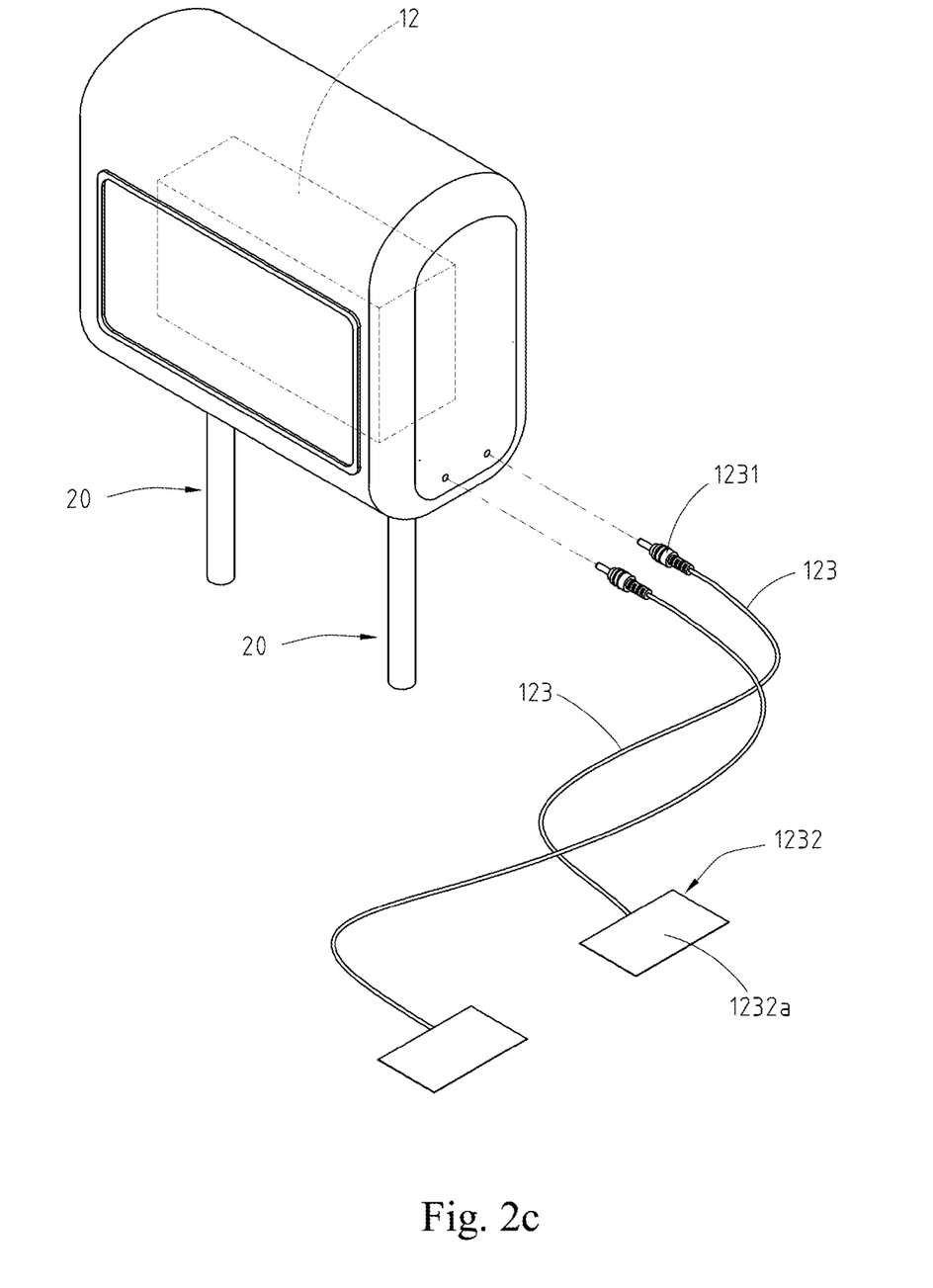
FIG. 2c is a perspective view (2) of the first embodiment of the headrest structure according to the instant disclosure.

While the details about the electroshock module 121 and the control module 122 are already described in the preceding paragraphs, hereinafter only the auxiliary electroshock member 123 is described. The auxiliary electroshock member 123 comprises at least one connecting end 1231 and at least one working end 1232, the connecting end 1231 is detachably and electrically connected to the electroshock module 121; for example, as shown in FIG. 2*b* and FIG. 2*c*, the connecting end 1231 is a terminal structure to be inserted into an inserting hole of the electroshock module 121, but embodiments are not limited thereto. The working end 1232 has an electroshock attaching plate 1232*a* provided for contacting the electroshock point of the heart of the patient, and the electroshock signal is delivered to the electroshock point of the heart of the patient through the electroshock attaching plate 1232*a* of the working end 1232. Additionally, the auxiliary electroshock member 123 can be received in the headrest structure 100 when not in use, so as not to affect the comfort of the user who leans against it.

Figure 3:
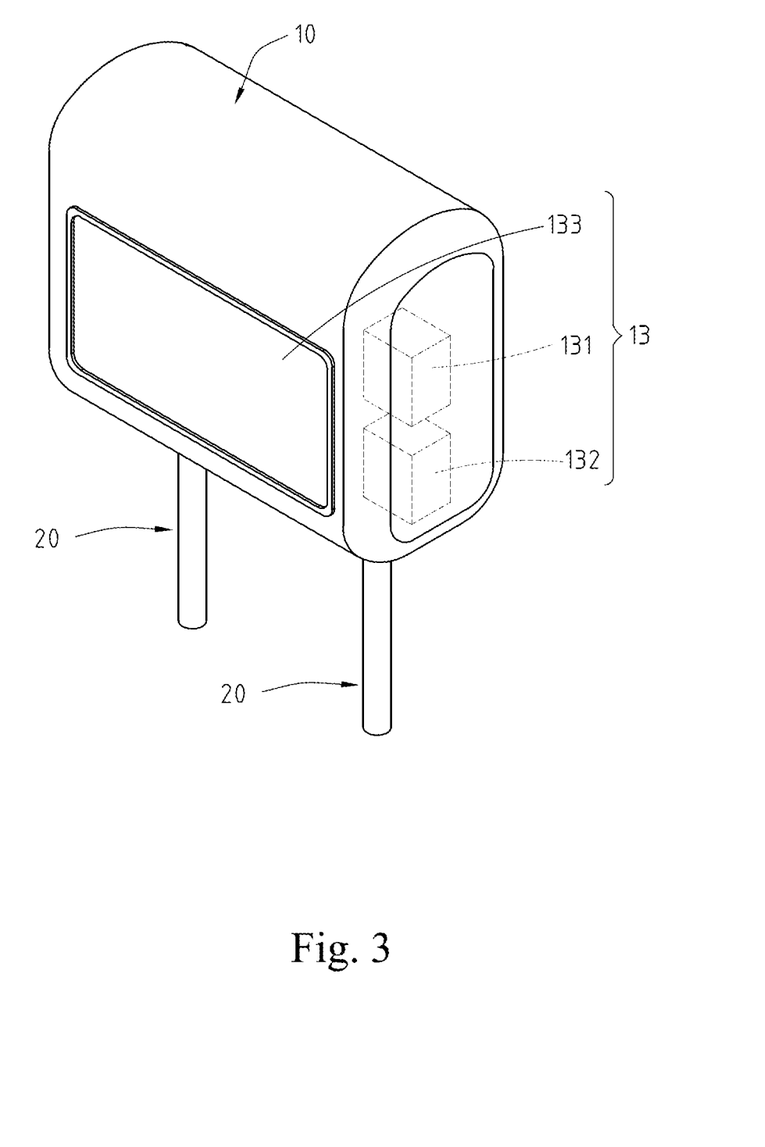
FIG. 3 is a perspective view (3) of the first embodiment of the headrest structure according to the instant disclosure.

In some implementation aspects, please refer to FIG. 3, showing a perspective view (3) of the first embodiment of the headrest structure 100 according to the instant disclosure. Here, the body 10 further comprises a display module 13 electrically connected to the AED 12 to selectively display at least one physiological parameter of the patient, at least one output parameter of the electroshock signal or the combination thereof (for example, the display module 13 displays the breath frequency, the blood pressure, the heartbeat, the temperature, the electrocardiogram or other physiological parameters of the patient). Here, the display module 13 is an LCD screen so as to display the aforementioned parameters numerically or graphically, so that the instant physiological condition of the patient can be conceived, but embodiments are not limited thereto. Additionally, here, the number of the display module 13 is one, but embodiments are not limited thereto. It is understood that, in some implementation aspects, the display module 13 is combined with the operating module of the control module 122; that is, the display module 13 is provided with touch-control function so that the user inputs the aforementioned parameters via the display module 13. In some implementation aspects, the display module 13 comprises a signal receiving unit 131, a coding-decoding unit 132 and a screen 133. The signal receiving unit 131 may be a wireless signal receiving unit, but embodiments are not limited thereto. Accordingly, the coding-decoding unit 132 converts a signal received by the signal receiving unit 131 into a video signal to display on the screen 133. Here, the signal receiving unit 131 is a wireless signal receiving unit; in other words, the display module 13 is provided with multimedia function, thereby the user can watch the video information converted from wireless signals received by the signal receiving unit 131 or the video information from internet streaming when the headrest structure 100 is assembled to the seat. Conversely, when someone encounters sudden cardiac arrest and needs proper treatments, the display module 13 can thus show the physiological information of the patient, the output parameters of the electroshock signal or other information regarding the patient. Additionally, in some implementation aspects, the headrest structure 100 further comprises a processor and a storage unit; the processor and the storage unit can signally connected to the display module 13. The storage unit may be a hard disk, a flash memory or a memory card. The processor can execute an application program. The application program is stored in the storage unit in advance or is downloaded from the internet and then stored in the storage unit. Based on this, the display module 13 displays the execution frames of the application program, and the application program can be controlled by the aforementioned operating module. For example, the application program may be a computer game, but embodiments are not limited thereto.

Figure 4A:
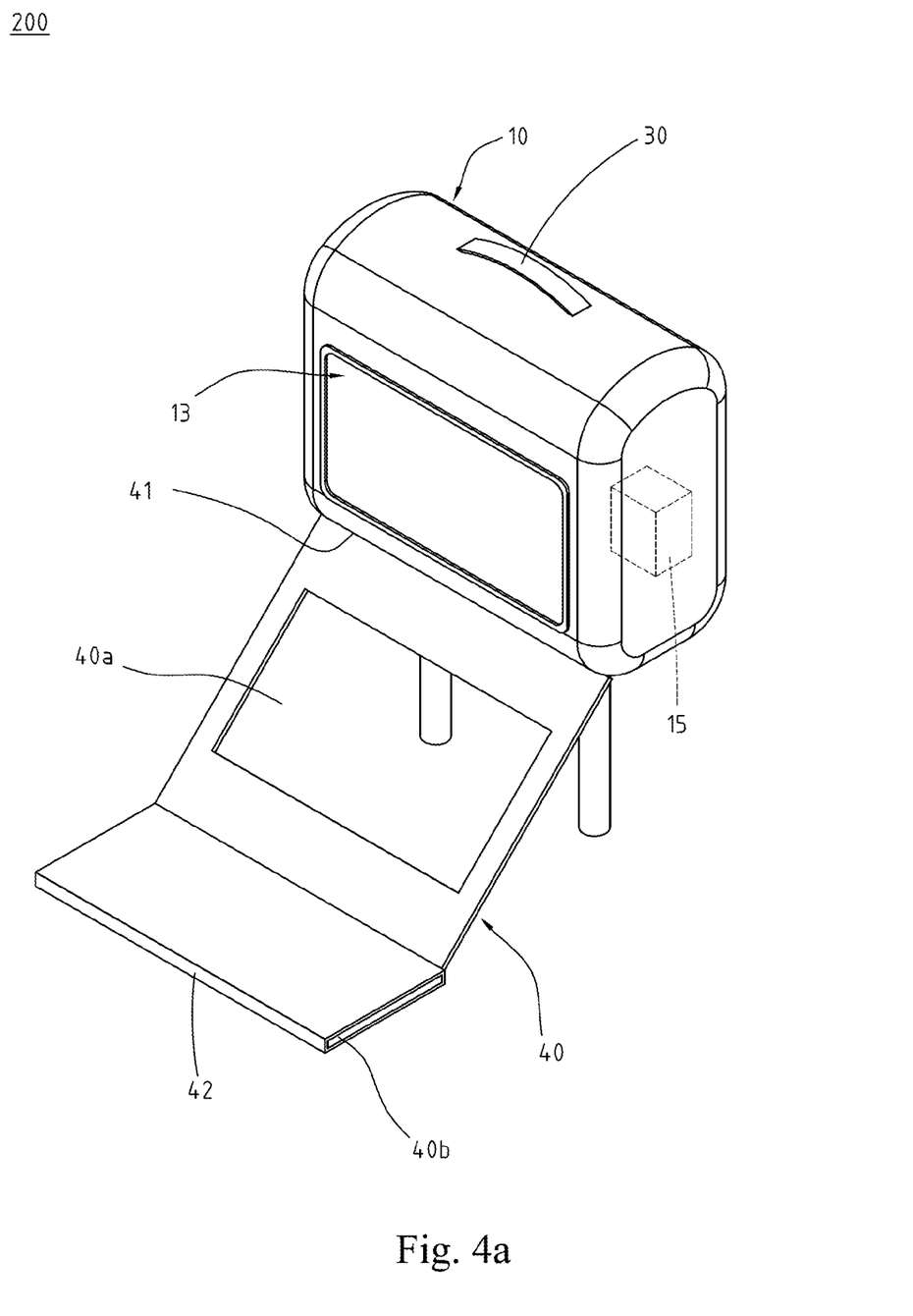
FIG. 4a is a perspective view (1) of a second embodiment of a headrest structure according to the instant disclosure.
Figure 4B:
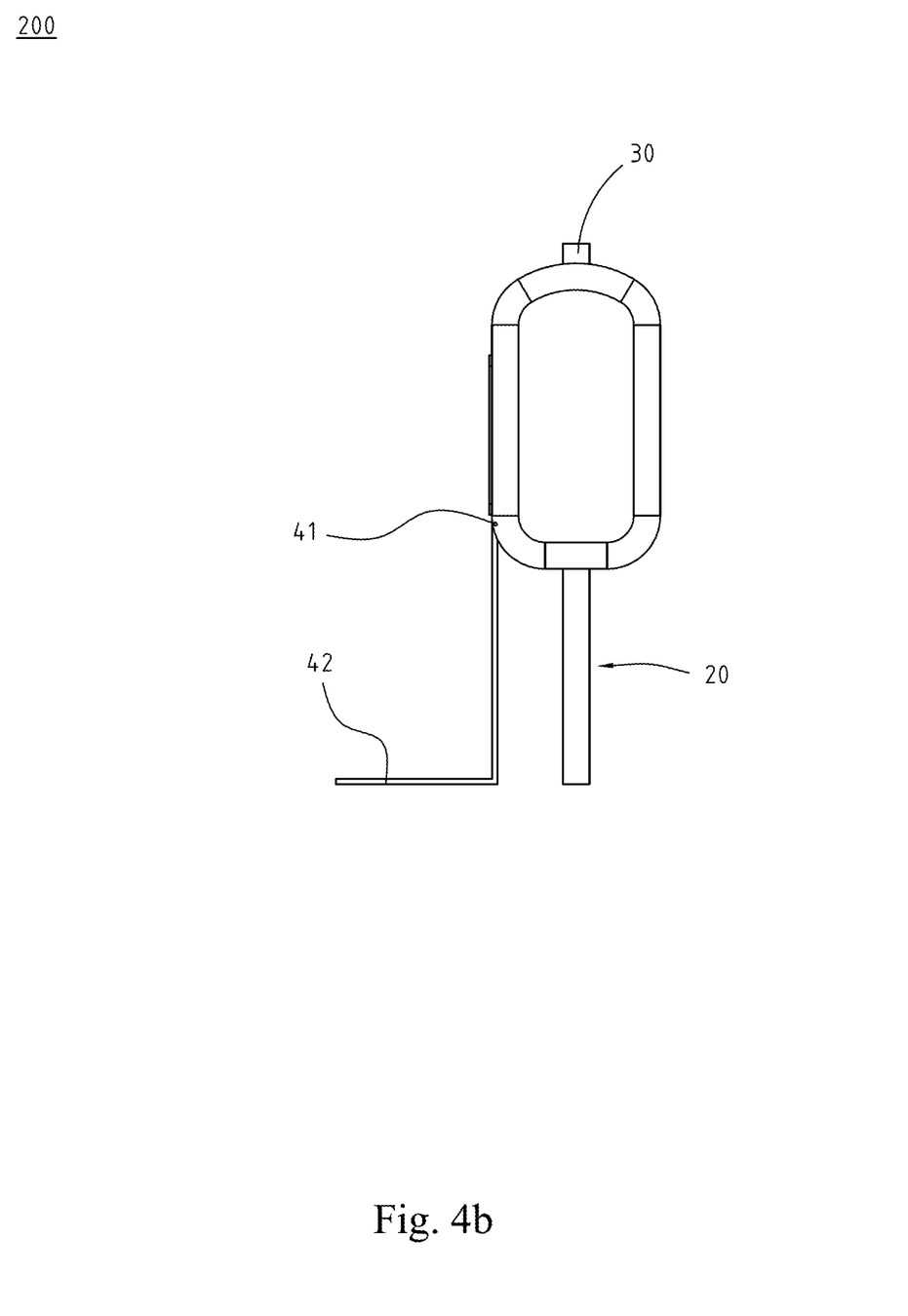
FIG. 4b is an operational view of the second embodiment of the headrest structure according to the instant disclosure.

Please refer to FIG. 4*a* to FIG. 4*e*, illustrating a second embodiment of a headrest structure 200 according to the instant disclosure. The structure of the second embodiment of the headrest structure 200 is approximately the same as that of the first embodiment, except that the second embodiment of the headrest structure 200 further comprises a handle 30 disposed on the body 10 and opposite to the supporting rods 20. Consequently, when necessary, the user can detach the headrest structure 200 from the seat of the transportation and carry the headrest structure 200 by holding the handle 30 so as to improve the mobility of the AED 12 of the headrest structure 200. Additionally, here, the headrest structure 200 further comprises a shielding member 40. The shielding member 40 comprises a pivoting portion 41 and an abutting portion 42 opposite to the pivoting portion 41. The pivoting portion 41 is pivoted on the body 10 and near to the supporting rods 20. Hence, when the shielding member 40 is located at a shielding position, the shielding member 40 shields the handle 30. While when the shielding member 40 is located at an open position, the handle 30 is exposed to outside with the abutting portion 42 and the combining ends 22 being coplanar so as to support the body 10 to stand on the ground (as shown in FIG. 4*b*).

Here, the shielding member 40 may be, but not limited to, a unitary member or a multi-piece member. In some implementation aspects, when the shielding member 40 shields the handle, the shielding member 40 also encloses the display module 13, but embodiments are not limited thereto. In some other implementation aspects, the shielding member 40 is substantially a frame structure and a window 40*a* (as shown in FIG. 4*a*), is defined thereon to correspond to the display module 13. Based on this, when the shielding member 40 shields the handle 30, the display module 13 is exposed to outside through the window 40*a* so that the user can still operate the display module 13. On the contrary, when the shielding member 40 is located at the open position, the abutting portion 42 and the combining ends 22 of the supporting rods 20 are coplanar so as to support the body 10. Therefore, the headrest structure 200 can be steadily placed on a desk or on the ground via the abutting portion 42 and the combining ends 22, thereby allowing the headrest structure 200 being placed stably after detaching from the seat. Additionally, after the headrest structure 200 is detached from the seat, the headrest structure 200 can still function as a multimedia player with the abutting portion 42 and the combining ends 22 being the support of the body 10. It is understood that, the abutting portion 42 of the shielding member 40 is not limited to a rectangular plate, but may be other structures with supporting function. In addition, as shown in FIG. 4a, in some implementation aspects, the shielding member 40 defines a receiving cavity 40b therein for receiving the auxiliary electroshock member 123, the manual of the AED 12, or other articles. In this embodiment, the receiving cavity 40b is close to the abutting portion 42. Alternatively, the receiving cavity 40b may be configured at the position where the window 40a is located.

Figure 4C:
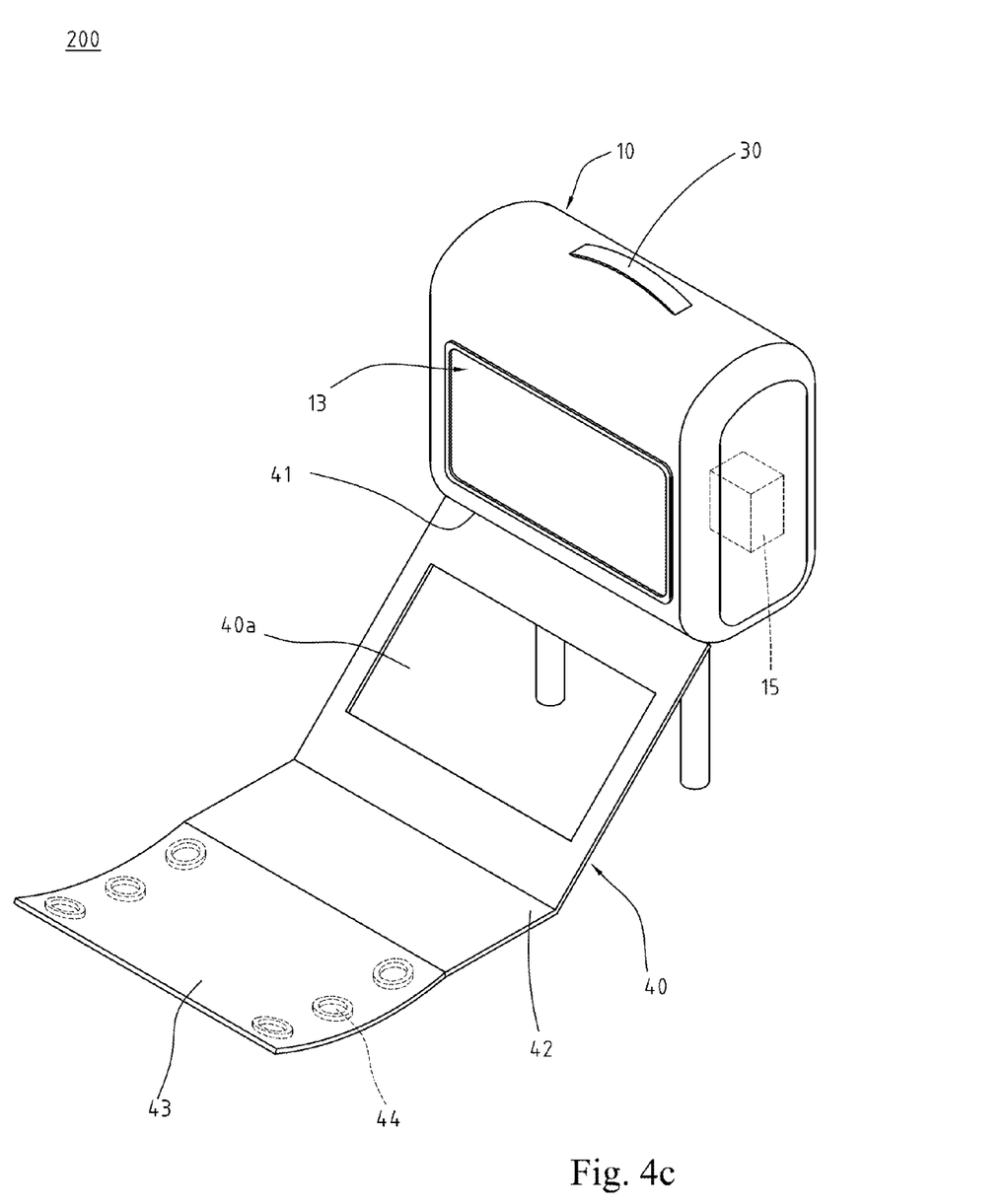
FIG. 4c is a perspective view (2) of the second embodiment of the headrest structure according to the instant disclosure.
Figure 4D:
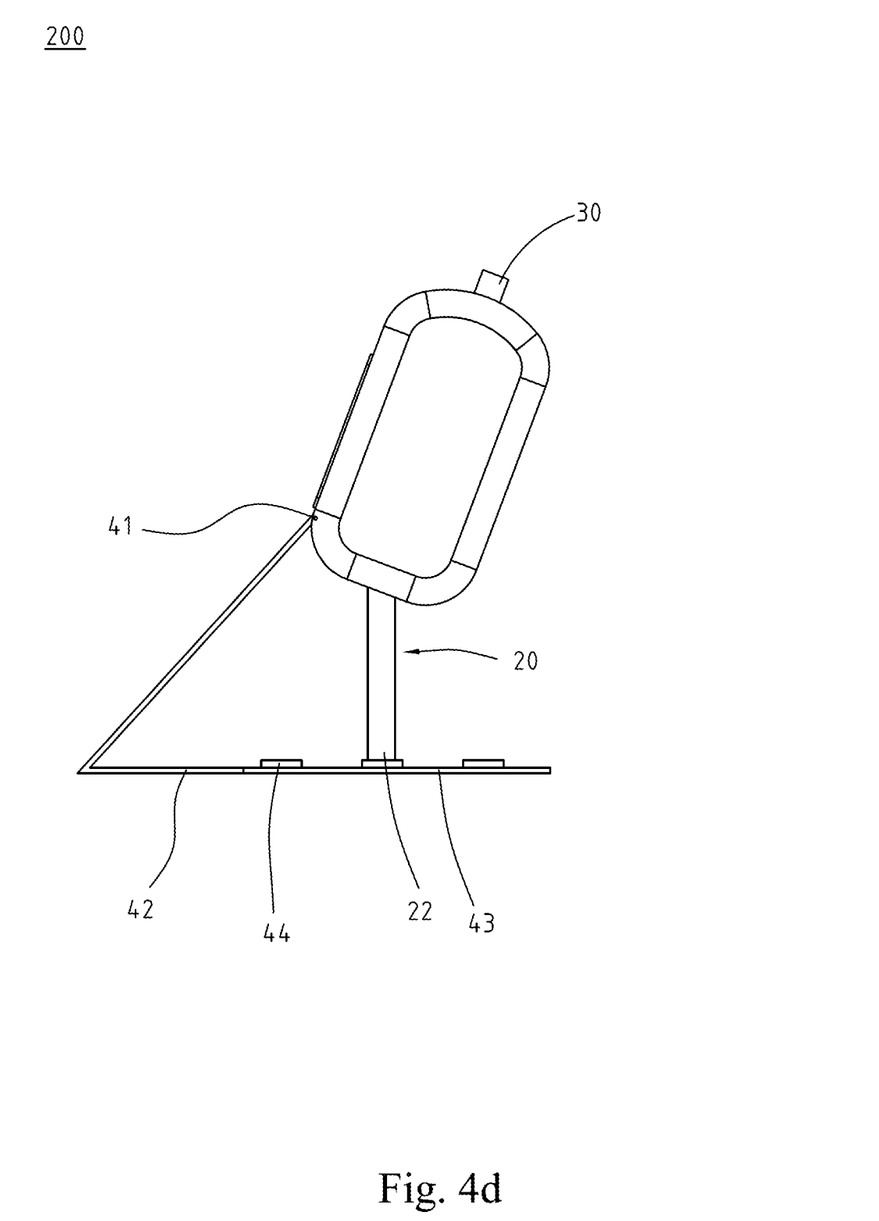
FIG. 4d is an operational view (1) of the headrest structure shown in FIG. 4c.
Figure 4E:
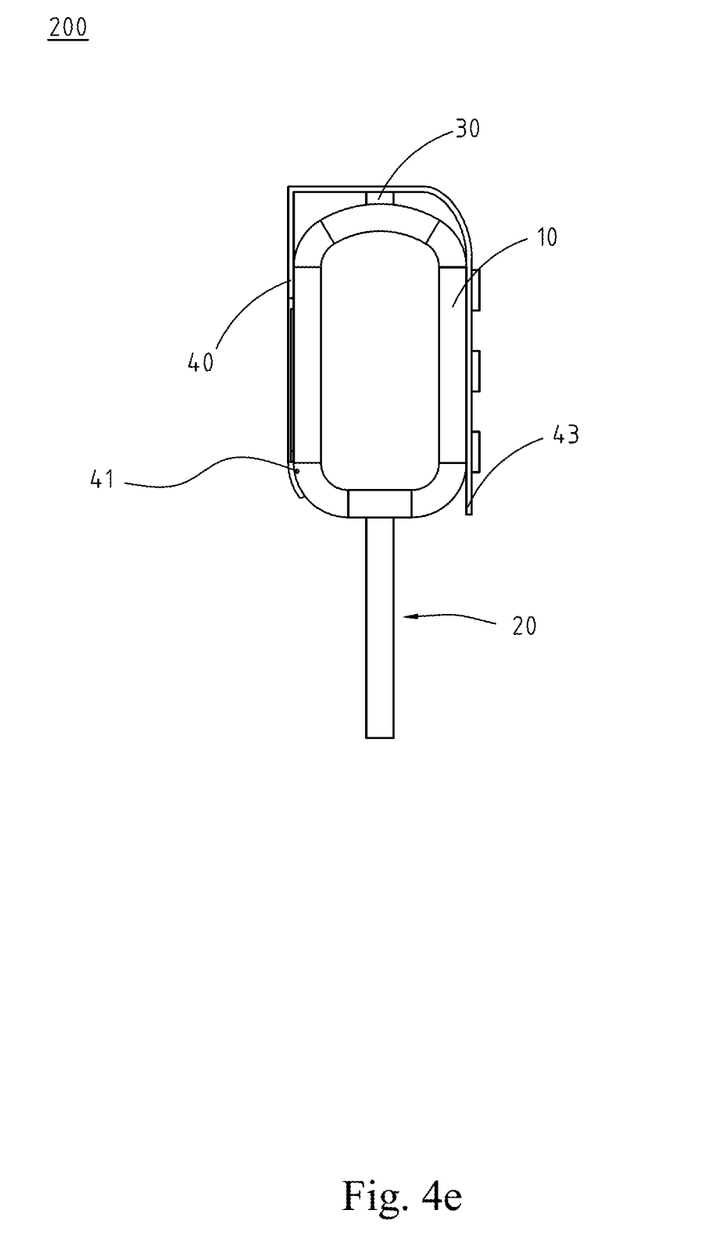
FIG. 4e is an operational view (2) of the headrest structure shown in FIG. 4c.

Please refer to FIG. 4c to FIG. 4e, in some implementation aspects, the headrest structure 200 further comprises a covering member 43 detachably or fixedly connected to the end portion of the abutting portion 42 of the shielding member 40. In this embodiment, the covering member 43 is fixedly connected to the end portion of the abutting portion 42 and the covering member 43 is made of soft materials. For example, the covering member 43 may be, but not limited to, made of cotton cloths, artificial cloths, leathers, or soft plastics. As shown in FIG. 4e, when the shielding member 40 is located at the shielding position to shield the handle 30, the covering member 43 would further cover on one side of the body 10 and opposite to the shielding member 40. Therefore, the covering member 43 would provide a better comfortable feeling and a better warming function when a user's head is leaned on the headrest structure 200. Besides, the covering member 43 can be provided for protecting the body so at to extend the usage life of the body 10 and can be provided for improving the beauty of the headrest structure 200. On the other hand, as shown in FIG. 4d, when the shielding member 40 is located at the open position to expose the handle 30, the abutting portion 42 and the combining ends 22 are coplanar so as to support the body 10 to stand on the covering member 43. In other words, when the shielding member 40 is located at the open position, the outer surface of the covering member 43 is in contact with the combining ends 22 and provides enough friction for steadily positioning the combining ends 22, such that the combining ends 22 and the abutting portions 42 stably support the body 10 to stand on the covering member 43. When the headrest structure 200 is placed on an uneven surface, the covering member 43 is placed on the uneven surface with the combining ends 22 disposed on the covering member 43 so as to support the body 10 stably. Furthermore, as shown in FIG. 4d, the headrest structure 200 further comprises at least one buckling member 44 disposed at the outer surface of the covering member 43 and corresponding to the combining ends 22 of the supporting rods 20. In this embodiment, two rows of buckling members 44 are assembled to the outer surface of the covering member 43, and the distance between the two rows is substantially equal to the distance between the two supporting rods 20. Therefore, when the shielding member 40 is located at the open position, the combining ends 22 are respectively held by the buckling members 44, but embodiments are not limited thereto. As shown in FIG. 4c, in this embodiment, the buckling members 44 are assembled in the covering member 43. Here, since the covering member 43 is made of soft materials, the buckling members 44 can effectively position the combining ends 22 of the supporting rods 20 even when the buckling members 44 are assembled in the covering member 43. Besides, the display angle of the display module 13 can be adjusted for various operational conditions by configuring the combining ends 22 of the supporting rods 20 with different buckling members 44.

Additionally, please refer to FIG. 4a, FIG. 4b and FIG. 4c again; in which embodiment, the body 10 further comprises a signal emitting member 15 electrically connected to the AED 12. In an implementation aspect, the signal emitting member 15 automatically emits a signal to rescue personnel upon the AED 12 is operating, so that the rescue personnel will arrive at the place where the signal is emitted from as soon as possible, but embodiments are not limited thereto. In some implementation aspects, the signal emitting member 15 is not linked to the AED 12 but linked to a switch (not shown), disposed on the headrest structure 200, so that the user directly operates the switch to launch the signal emitting member 15 for emitting the signal and does not launch the signal emitting member 15 by mistake upon operating the AED 12. Here, the signal emitted by the signal emitting member 15 is a wireless electric wave signal, but is not limited thereto. In practice, when a patient encounters a sudden cardiac arrest, a user can use the signal emitting member to send rescue signals to a non-specific third party (e.g., a medical institute, an insurance company, a rescue team, etc.), such that the third party would instantly deliver the message to a professional rescue team, and the team can arrive the place where the rescue signals are emitted from as soon as possible and apply proper treatments to the patient.

In some embodiments, the signal receiving unit 131 may be provided for receiving an external operation signal sent from a non-specific third party. In other words, when the user cannot operate the AED 12 by himself or herself, the AED 12 can be remotely controlled by the external operation signal. On the other hand, the signal receiving unit 131 may be provided for receiving an external guiding message. The external guiding message comprises a video file or a video stream adapted to be displayed on the screen 133 or adapted to be delivered to the user through the speaker in the display module 13. Therefore, the user may operate the AED 12 according to the external guiding message. For example, when the user cannot operate the AED 12 by himself or herself, the user can trigger the signal emitting member 15 so as to telecommunicate with or signally connect to a non-specific third party. Then, the third party can explain the operation of the AED 12 orally and the voice of the third party would be delivered to the user through the speaker in the display module 13, and then the user would realize how to operate the AED 12. Alternatively, the third party can demonstrate how to operate the AED 12, and the demonstration would be instantly sent to the user in a video file format or a video stream format to allow the user knowing the operation of the AED 12.

In one embodiment, the supporting rods 20 may be coupled to the signal receiving unit 131 and/or the signal emitting member 15 to be the antenna of the signal receiving unit 131 or the antenna of the signal emitting member 15. That is, the whole supporting rods 20 may be made of metal and acted as radiation bodies for sending wireless signals. Alternatively, in some embodiments, parts of the supporting rods 20 are made of metal and acted as antenna. In addition, based on the frequency of operation and the radiation pattern, the metal part of the supporting rods 20 may have different shapes. In some embodiments, the signal receiving unit 131 and the signal emitting member 15 may be integrated as a single circuit or a single chip.

In conclusion, with the headrest structure according to the instant disclosure, when somebody suddenly suffers ventricular fibrillation or the ventricular tachycardia, another person (whether their friend or rescue personnel), can use the AED in the headrest structure to apply electroshock to the patient's heart, followed by applying external cardiac massage procedures or other cardiopulmonary resuscitation procedures to give the patient first aid treatment, under which circumstances the patient's likelihood of survival are increased significantly due to proper treatment being applied to the patient before arriving in the emergency room.

In addition, the headrest structure can be recharged by the power sources from the transportation at where the headrest structure is located. Further, when the headrest structure is not in use, the headrest structure can be detached from the transportation for being utilized to another carrier, for storing properly, or for performing maintenance thereto.

While the instant disclosure has been described by the way of example and in terms of the preferred embodiments, it is to be understood that the invention need not be limited to the disclosed embodiments. On the contrary, it is intended to cover various modifications and similar arrangements included within the spirit and scope of the appended claims, the scope of which should be accorded the broadest interpretation so as to encompass all such modifications and similar structures.

What is claimed is:

1. A headrest structure, comprising:
   a body, comprising:
      a covering cushion; and
      an automated external defibrillator, enclosed by the covering cushion and opposite to a leaning surface of the body adapted for head leaning; and
   two supporting rods, each of the supporting rods comprising a linking end and a combining end opposite to the linking end, each of the supporting rods connected to the body with the linking end so as to support the body.

2. The headrest structure according to claim 1, further comprising a handle disposed on the body and opposite to the supporting rods.

3. The headrest structure according to claim 2, wherein the automated external defibrillator comprises:
   an electroshock module, provided to output an electroshock signal;
   at least one auxiliary electroshock member, comprising at least one connecting end and at least one combining end, the connecting end is detachably and electrically connected to the electroshock module, the working end is provided to contact with an electroshock point of the heart of a patient, the electroshock signal is delivered to the electroshock point of the heart of the patient through the working end; and
   a control module, electrically connected to the electroshock module to control the output of the electroshock signal.

4. The headrest structure according to claim 2, wherein the body further comprises a signal emitting member electrically connected to the automated external defibrillator, so that the signal emitting member automatically emits an electronic signal when the automated external defibrillator starts operation.

5. The headrest according to claim 2, wherein the body further comprises a signal emitting member provided for emitting an electronic signal.

6. The headrest structure according to claim 1, further comprising a shielding member, the shielding member comprising a pivoting portion and an abutting portion opposite to the pivoting portion, the pivoting portion pivoted on the body and near to the supporting rods, wherein, when the shielding member is located at an open position, the abutting portion and the combining ends are coplanar so as to support the body.

7. The headrest structure according to claim 6, further comprising a covering member connected to an end portion of the abutting portion, wherein when the shielding member is located at a shielding position, the covering member is covered on one side of the body and opposite to the shielding member, wherein when the shielding member is located at the open position, the abutting portion and the combining ends are coplanar so as to support the body to stand on the covering member.

8. The headrest according to claim 7, further comprising at least one buckling member disposed at the covering member and corresponding to the combining ends of the supporting rods.

9. The headrest structure according to claim 8, wherein the automated external defibrillator comprises:
   an electroshock module, provided to output an electroshock signal;
   at least one auxiliary electroshock member, comprising at least one connecting end and at least one combining end, the connecting end is detachably and electrically connected to the electroshock module, the working end is provided to contact with an electroshock point of the heart of a patient, the electroshock signal is delivered to the electroshock point of the heart of the patient through the working end; and
   a control module, electrically connected to the electroshock module to control the output of the electroshock signal.

10. The headrest structure according to claim 8, wherein the body further comprises a signal emitting member electrically connected to the automated external defibrillator, so that the signal emitting member automatically emits an electronic signal when the automated external defibrillator starts operation.

11. The headrest according to claim 8, wherein the body further comprises a signal emitting member provided for emitting an electronic signal.

12. The headrest structure according to claim 7, wherein the automated external defibrillator comprises:
   an electroshock module, provided to output an electroshock signal;
   at least one auxiliary electroshock member, comprising at least one connecting end and at least one combining end, the connecting end is detachably and electrically connected to the electroshock module, the working end is provided to contact with an electroshock point of the heart of a patient, the electroshock signal is delivered to the electroshock point of the heart of the patient through the working end; and
   a control module, electrically connected to the electroshock module to control the output of the electroshock signal.

13. The headrest structure according to claim 7, wherein the body further comprises a signal emitting member electrically connected to the automated external defibrillator, so that the signal emitting member automatically emits an electronic signal when the automated external defibrillator starts operation.

14. The headrest according to claim 7, wherein the body further comprises a signal emitting member provided for emitting an electronic signal.

15. The headrest structure according to claim 6, wherein the automated external defibrillator comprises:

an electroshock module, provided to output an electroshock signal;

at least one auxiliary electroshock member, comprising at least one connecting end and at least one combining end, the connecting end is detachably and electrically connected to the electroshock module, the working end is provided to contact with an electroshock point of the heart of a patient, the electroshock signal is delivered to the electroshock point of the heart of the patient through the working end; and a control module, electrically connected to the electroshock module to control the output of the electroshock signal.

16. The headrest structure according to claim 15, wherein the body further comprises a display module electrically connected to the automated external defibrillator, the display module selectively displays at least one physiological parameter of the patient, at least one output parameter of the electroshock signal or the combination thereof.

17. The headrest structure according to claim 16, wherein the display module comprises a signal receiving unit, a coding-decoding unit and a screen, the coding-decoding unit converts a signal received by the signal receiving unit into a video signal to display on the screen.

18. The headrest structure according to claim 17, wherein the supporting rods are coupled to the signal receiving unit to be an antenna of the signal receiving unit.

19. The headrest structure according to claim 6, wherein the body further comprises a signal emitting member electrically connected to the automated external defibrillator, so that the signal emitting member automatically emits an electronic signal when the automated external defibrillator starts operation.

20. The headrest according to claim 6, wherein the body further comprises a signal emitting member provided for emitting an electronic signal.

21. The headrest structure according to claim 1, wherein the automated external defibrillator comprises:

an electroshock module, provided to output an electroshock signal;

at least one auxiliary electroshock member, comprising at least one connecting end and at last one combining end, the connecting end is detachably and electrically connected to the electroshock module, the working end is provided to contact with an electroshock point of the heart of a patient, the electroshock signal is delivered to the electroshock point of the heart of the patient through the working end; and a control module, electrically connected to the electroshock module to control the output of the electroshock signal.

22. The headrest structure according to claim 1, wherein the body further comprises a signal emitting member electrically connected to the automated external defibrillator, so that the signal emitting member automatically emits an electronic signal when the automated external defibrillator starts operation.

23. The headrest structure according to claim 22, wherein the supporting rods are coupled to the signal emitting member to be an antenna of the signal emitting member.

24. The headrest according to claim 1, wherein the body further comprises a signal emitting member provided for emitting an electronic signal.

25. The headrest structure according to claim 24, wherein the supporting rods are coupled to the signal emitting member to be an antenna of the signal emitting member.

* * * * *